(12) United States Patent
Katz (10) Patent No.: US 9,672,755 B2
(45) Date of Patent: Jun. 6, 2017

(54) SYSTEM AND METHOD FOR REWARDING A CHILD FOR BEHAVING WELL WHILE DINING

(71) Applicant: Liran Katz, Rishon le Zion (IL)

(72) Inventor: Liran Katz, Rishon le Zion (IL)

(73) Assignee: Liran Katz, Rishon le Zion (IL)

( * ) Notice: Subject to any disclaimer, the term of this patent is extended or adjusted under 35 U.S.C. 154(b) by 0 days.

(21) Appl. No.: 15/266,810

(22) Filed: Sep. 15, 2016

(65) Prior Publication Data

US 2017/0084192 A1    Mar. 23, 2017

Related U.S. Application Data

(60) Provisional application No. 62/220,473, filed on Sep. 18, 2015.

(51) Int. Cl.
*G09B 19/00* (2006.01)
*G09B 5/00* (2006.01)
*A61B 5/00* (2006.01)
*G01G 19/52* (2006.01)

(52) U.S. Cl.
CPC .............. *G09B 19/00* (2013.01); *G01G 19/52* (2013.01); *G09B 5/00* (2013.01); *A61B 5/00* (2013.01)

(58) Field of Classification Search
None
See application file for complete search history.

(56) References Cited

U.S. PATENT DOCUMENTS

| 2,213,837 A * | 9/1940 | Gill ................. A47G 19/02 126/246 |
| 2,322,665 A | 6/1943 | Ryan et al. |
| 2,561,594 A | 7/1951 | Harry et al. |
| 4,676,328 A | 6/1987 | Morino |
| 5,294,172 A | 3/1994 | Dubus |
| 5,817,006 A | 10/1998 | Bergh et al. |
| 6,352,258 B1 | 3/2002 | Fitzgerald et al. |
| 6,541,713 B2 | 4/2003 | White |
| 8,061,300 B2 * | 11/2011 | McElroy, Jr. ........ A01K 1/0107 119/164 |
| 8,127,605 B2 | 3/2012 | Kolada et al. |
| 8,175,746 B2 | 5/2012 | Godlewski |

(Continued)

*Primary Examiner* — Sam Yao
*Assistant Examiner* — Daniel Lane
(74) *Attorney, Agent, or Firm* — Active Knowledge Ltd.

(57) ABSTRACT

Systems and methods for rewarding a child for behaving well while dining. One embodiment includes the steps of: generating indications proportional to the weight of food on a plate, calculating the rate of removing the food from the plate ($R_r$), and comparing $R_r$ with a predetermined max eating rate ($R_m$). When $R_r < R_m$ commanding a container, which stores a reward for the child, to switch from a closed state to an open state when the weight of the food on the plate reaches below a predetermined threshold. And when $R_r > R_m$ not commanding the container to switch from the closed state to the open state when the weight of the food on the plate reaches below the predetermined threshold.

18 Claims, 8 Drawing Sheets

(56) References Cited

U.S. PATENT DOCUMENTS

| | | |
|---|---|---|
| 8,585,409 B1 * | 11/2013 | Haywood .......... G09B 19/0076 |
| | | 434/127 |
| 8,672,504 B2 | 3/2014 | Kramer |
| 8,893,911 B2 | 11/2014 | Damaghi et al. |
| 8,969,744 B2 | 3/2015 | He |
| 9,169,671 B1 | 10/2015 | Collins et al. |
| 9,314,206 B2 | 4/2016 | Menczel et al. |
| 2002/0079142 A1 | 6/2002 | White |
| 2006/0219187 A1 * | 10/2006 | Krishnamurthy .... A01K 5/0275 |
| | | 119/719 |
| 2008/0000398 A1 | 1/2008 | Barkley |
| 2008/0113614 A1 * | 5/2008 | Rosenblatt ............. G06Q 30/06 |
| | | 455/3.05 |
| 2008/0280278 A1 | 11/2008 | Chu et al. |
| 2010/0327001 A1 | 12/2010 | Godlewski |
| 2011/0275040 A1 | 11/2011 | de La Torre Paniagua et al. |
| 2012/0135383 A1 | 5/2012 | Jang et al. |
| 2012/0183934 A1 | 7/2012 | Sodersten et al. |
| 2014/0058559 A1 * | 2/2014 | Haynes ................ A01K 5/0114 |
| | | 700/232 |
| 2015/0143750 A1 * | 5/2015 | Jalbert ..................... E06B 7/32 |
| | | 49/25 |

\* cited by examiner

SYSTEM AND METHOD FOR REWARDING A CHILD FOR BEHAVING WELL WHILE DINING

CROSS-REFERENCE TO RELATED APPLICATIONS

This Application claims the benefit of U.S. Provisional Patent Application Ser. No. 62/220,473, filed Sep. 18, 2015.

BACKGROUND

Parents usually need to struggle with their children until they eat their food. This struggle takes time and effort, may repeat frequently, and may not result in teaching the child to behave well while dining. The children may not want to eat their food because they want to do other things that appear more attractive to them. But as parents, we would like our children to eat with everyone around the table and to finish their food nicely.

So in many meals there are the same arguments and/or fights with the children about convincing them to eat their food. Parents usually use the "Carrot or Stick" approach, which refers to a policy of offering a combination of rewards and/or punishments to induce behavior. In the "stick" approach, the parent will sometimes say to the children that if they do not finish their food and do not behave well then they will not be allowed to watch TV today or play on the computer. In the "Carrot" approach, the parent will say to the children that if they finish the food and eat nicely then they will get a chocolate, a candy, a gift, a present, and/or a special surprise. This routine may repeat frequently, and eventually, at the end, the children receive the chocolate, candy or another reward.

Thus, there is a need for a system and a method to reward a child to eat well without throwing away the food, and without requiring the parents to invest so much time and energy in struggling and fighting until the child eats the dish.

SUMMARY

In one embodiment, in order to ease the above-described fight around the table, the parent locks a reward in a container that is to be opened automatically once the child finishes the food on his/her plate. The container may be transparent so the child can see the reward (chocolate, candy, gift, etc.), or it can be opaque to surprise the child once it is opened.

The container may have a shape of a box, optionally with a closing lid, and/or it can be shaped like a toy, such as a frog, a dog, an airplane, a Pac-Man, a seashell, etc. (all referred to as a container), which stores the reward and does not enable the child to see or get the reward in its closed state. Once the food is finished, the container will open automatically to enable the child to have the reward (such as a dessert or a gift) for eating well and finishing the food. Optionally, the container receives from the plate the weight of the food remaining on the plate. Additionally or alternatively, the container may as well show the child his/her progress towards getting the reward.

Optionally, the container does not switch to its open state when the weight of the food on the plate decreases faster than expected, because it probably means that the child either threw the food quickly from the plate without eating it, or flipped the plate upside down.

Children love to play and everything that involved with gaming, playing, winning, getting rewards at the end (either they know what the reward is, or may be better when it is a surprise) may motivate the children to finish their food and behave well around the dining table.

In one embodiment, the parent stores a reward in a closed container that is opened automatically after the child finishes the food on his/her plate. However, it is usually undesirable that the child will get used to throwing food out of the plate in order to receive the reward stored in the container. Thus, in order not to encourage the child to throw the food out of the plate, the system measures the rate of removing the food from the plate, and if the rate does not exceed a predetermined eating rate threshold, then the container is opened when the weight of the food on the plate reaches a predetermined threshold.

In one embodiment, a system configured to reward a child for behaving well while dining includes the following elements: A container configured to be in at least a closed state or an open state; whereby the container is configured to store a reward for the child, and the volume of the container in its closed state is at least 50 milliliter. A plate configured to hold food. A weighing module configured to generate indications proportional to the weight of the food on the plate. And a processor configured to receive the indications while the container is in its closed state, and to determine, based on analysis of the indications, whether to command the container to switch to its open state when the weight of the food on the plate reaches below a predetermined threshold.

Optionally, the analysis comprises calculating the rate of removing the food from the plate ($R_r$), the processor is further configured to compare $R_r$ with a predetermined max eating rate ($R_m$), when $R_r < R_m$ the processor commands the container to switch to its open state when the weight of the food on the plate reaches below the predetermined threshold, and when $R_r > R_m$ the processor does not command the container to switch to its open state when the weight of the food on the plate reaches below the predetermined threshold. Optionally, $R_m$ is set by at least one of the following: (i) $R_m$ is a function of the age of the child, (ii) $R_m$ is set by the child's parent via a user interface that communicates with the container, and (iii) further comprising a computer configured to receive, from a camera, a video of the child while eating from the plate, and to set $R_m$ according to the child's actual eating rate. Optionally, the processor is further configured to: receive data from a movement sensor coupled to the plate, identify flipping the plate based on the data, and not commanding the container to switch to its open state when the weight of the food on the plate reaches below the predetermined threshold. Optionally, the processor is further configured to: receive data from a movement sensor coupled to the plate, utilize the data to identify that the plate was not flipped while dining, and command the container to switch to its open state when the weight of the food on the plate reaches below the predetermined threshold. Optionally, the predetermined threshold is below at least one of the following: 100 gram, 20 gram, 50% of the initial weight of the food, and 10% of the initial weight of the food. Optionally, the plate and the container are stiffly connected as a single piece. Optionally, the plate and the container are two distinct devices that are not physically connected in a fixed manner. Optionally, the system further includes a tray configured to hold the plate; the tray comprises the weighing module, and the weighing module is configured to weigh the plate without the food, and then to weigh the plate with the food in order to calculate the indications. Optionally, the tray and the container are stiffly connected as a single piece. Optionally, the tray and the container are two distinct devices that are not physically connected in a fixed manner, and further comprising a short-range communication module configured to send data from the tray to the container. Optionally, the tray is integrated with a high chair.

In another embodiment, a method for rewarding a child for behaving well while dining includes the following steps: generating indications proportional to weight of food on a plate; calculating rate of removing the food from the plate ($R_r$); comparing $R_r$ with a predetermined max eating rate ($R_m$), when $R_r<R_m$ then commanding a container to switch from a closed state to an open state when the weight of the food on the plate reaches below a predetermined threshold, and when $R_r>R_m$ then not commanding the container to switch from the closed state to the open state when the weight of the food on the plate reaches below the predetermined threshold; whereby the container is configured to store a reward for the child, and the volume of the container in its closed state is at least 50 milliliter.

Optionally, the method further includes determining $R_m$ by at least one of the following: (i) determining $R_m$ as a function of the age of the child, (ii) determining $R_m$ by the child's parent via a user interface that communicates with the container, and (iii) further comprising receiving a video of the child while eating from the plate, and setting $R_m$ according to the child's actual eating rate. Optionally, the method further includes receiving data from a movement sensor coupled to the plate, identifying flipping the plate based on the data, and not commanding the container to switch from the closed state to the open state when the weight of the food on the plate reaches below the predetermined threshold. Optionally, the method further includes receiving data from a movement sensor coupled to the plate, utilizing the data to identify that the plate was not flipped while dining, and commanding the container to switch from the closed state to the open state when the weight of the food on the plate reaches below the predetermined threshold. Optionally, the method further includes a tray configured to hold the plate, wherein the tray is programmed to weigh the food on the plate by weighing the plate without the food and then weighing the plate with the food.

In still another embodiment, a system configured to reward a child for behaving well while dining includes the following elements: a container comprising an opening; a lid configured to cover or uncover the opening; a plate configured to hold food; a weighing module configured to generate indications proportional to the weight of the food on the plate; and a processor configured to receive the indications while the lid covers the opening, and to determine, based on analysis of the indications, whether to command a mechanism to move the lid to uncover the opening when the weight of the food on the plate reaches below a predetermined threshold.

Optionally, the analysis comprises calculating the rate of removing the food from the plate ($R_r$), the processor is further configured to compare $R_r$ with a predetermined max eating rate ($R_m$), when $R_r<R_m$ the processor commands the mechanism to move the lid to uncover the opening when the weight of the food on the plate reaches below a predetermined threshold, and when $R_r>R_m$ the processor does not command the mechanism to move the lid to uncover the opening when the weight of the food on the plate reaches below the predetermined threshold. Optionally, the processor is further configured to: receive data from a movement sensor coupled to the plate, identify flipping the plate based on the data, and not commanding the mechanism to move the lid to uncover the opening when the weight of the food on the plate reaches below the predetermined threshold.

BRIEF DESCRIPTION OF THE DRAWINGS

The embodiments are herein described by way of example only, with reference to the accompanying drawings. No attempt is made to show structural details of the embodiments in more detail than is necessary for a fundamental understanding of the embodiments. In the drawings.

DETAILED DESCRIPTION

Figure 1:
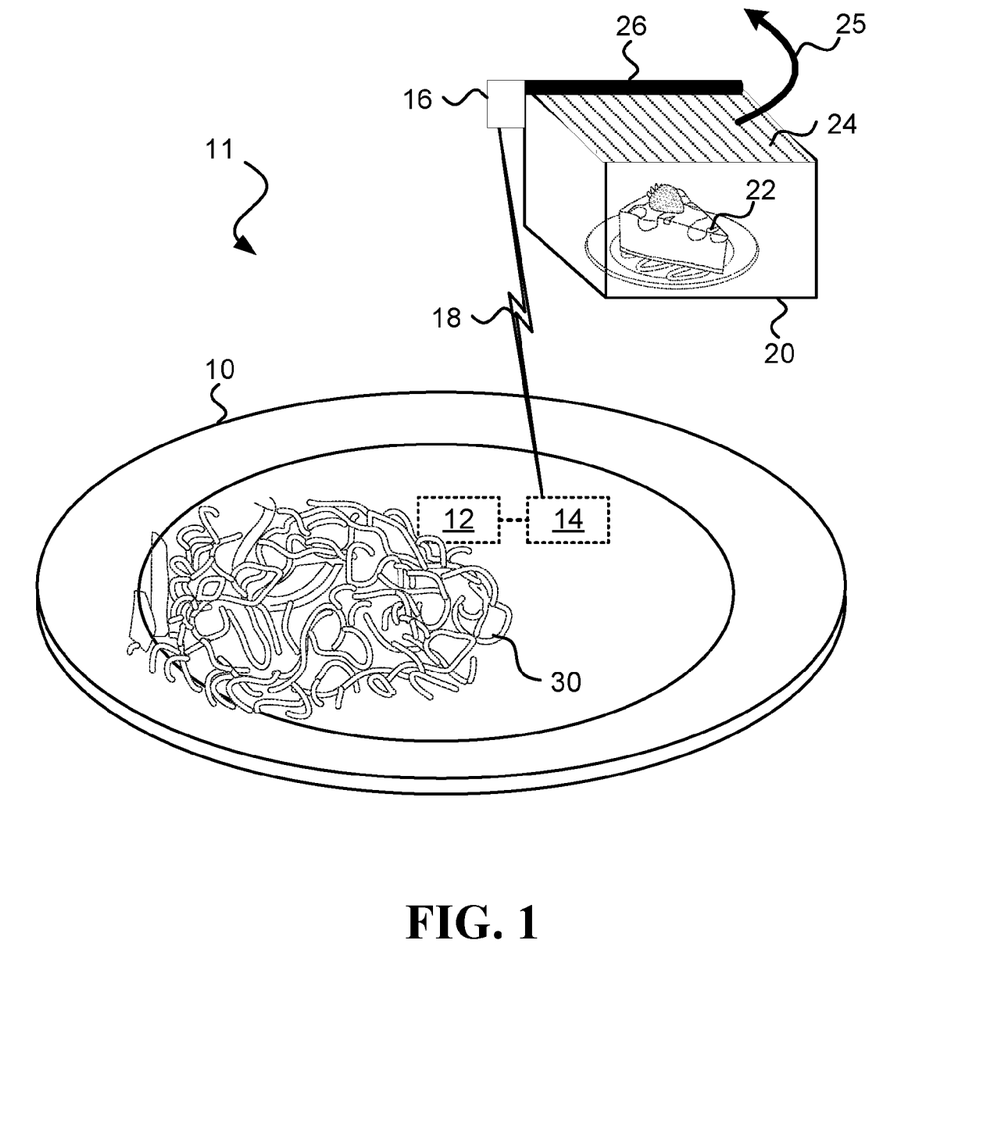
FIG. 1 illustrates one embodiment of a system that rewards a child for behaving well while dining.
Figure 6A:
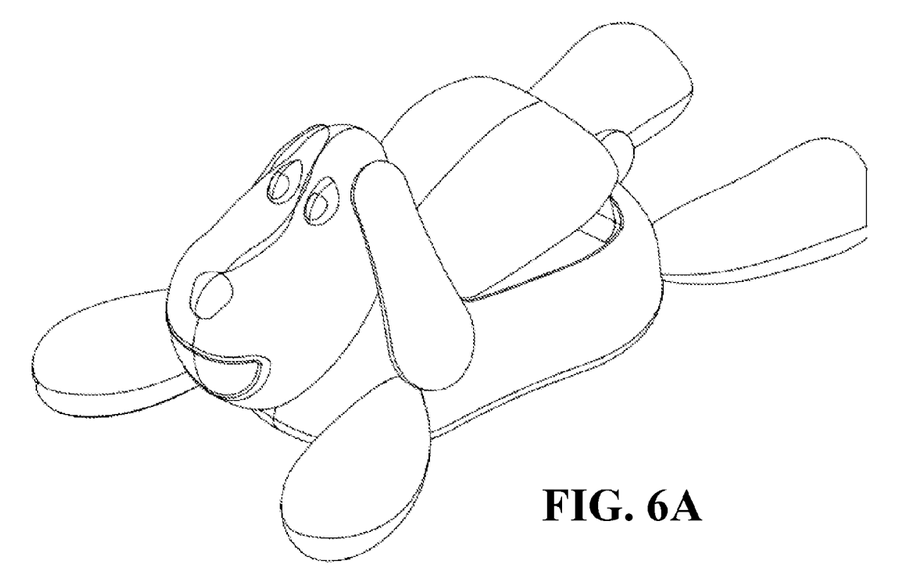
FIG. 6A and FIG. 6B illustrate a slightly opened dog-shaped container.
Figure 6B:
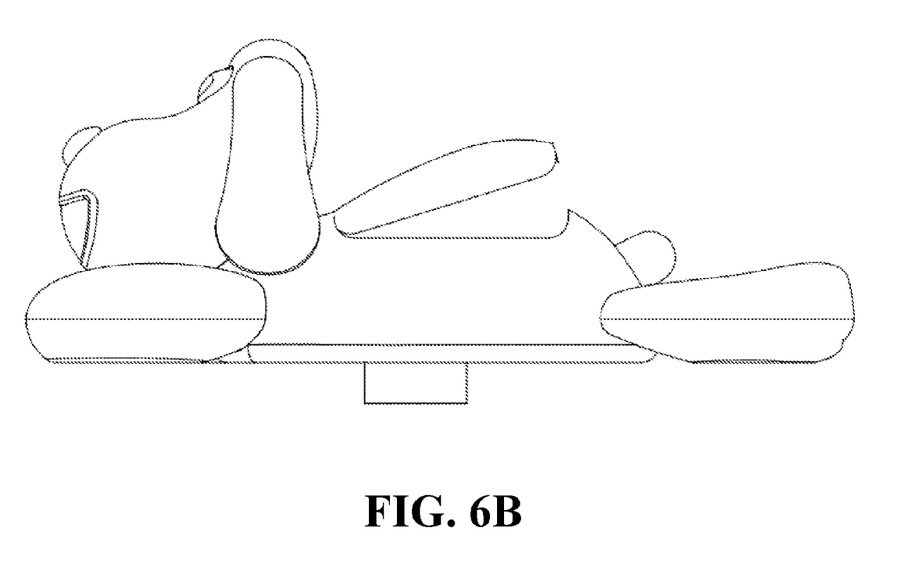
Figure 7A:
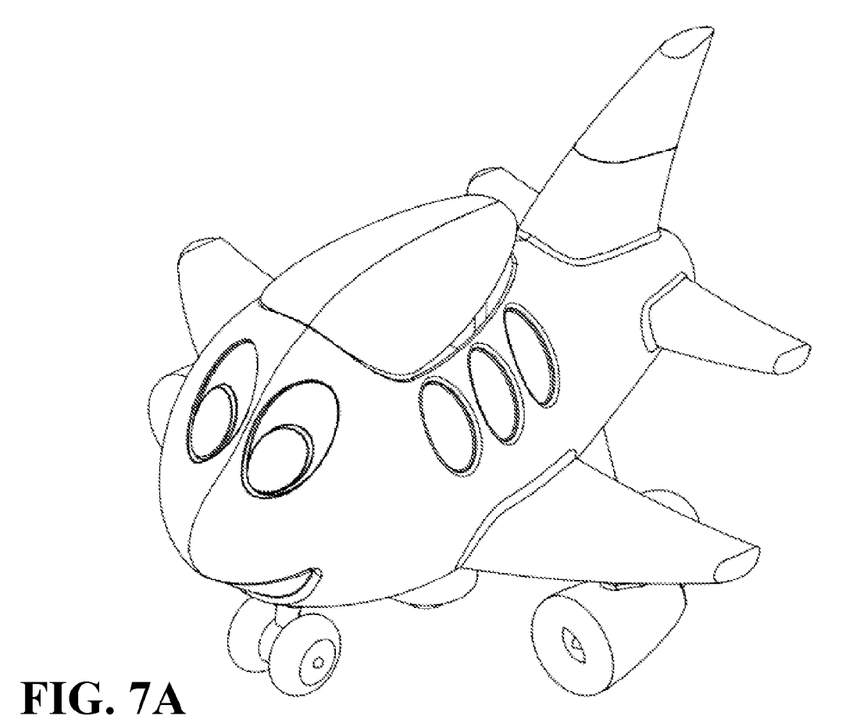
FIG. 7A and FIG. 7B illustrate a slightly opened airplane-shaped container.
Figure 7B:
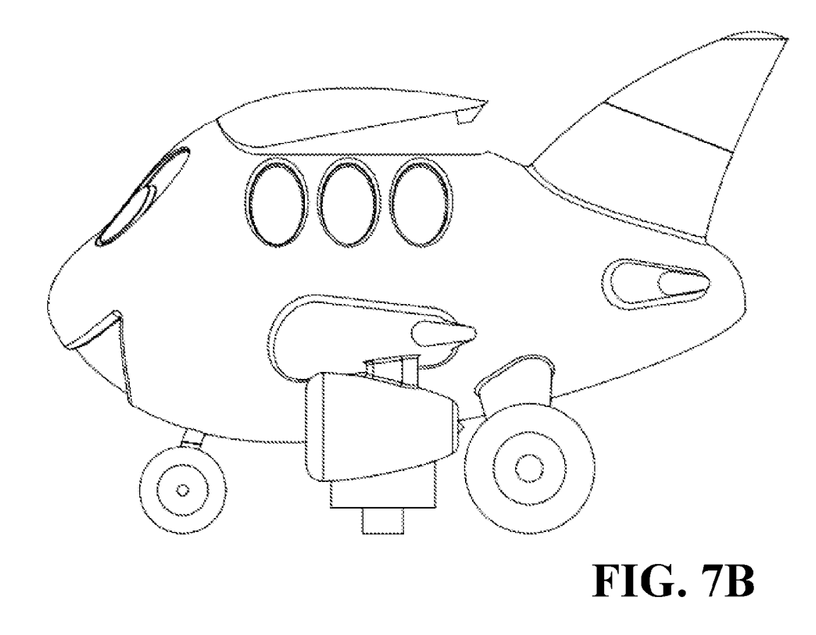
Figure 8A:
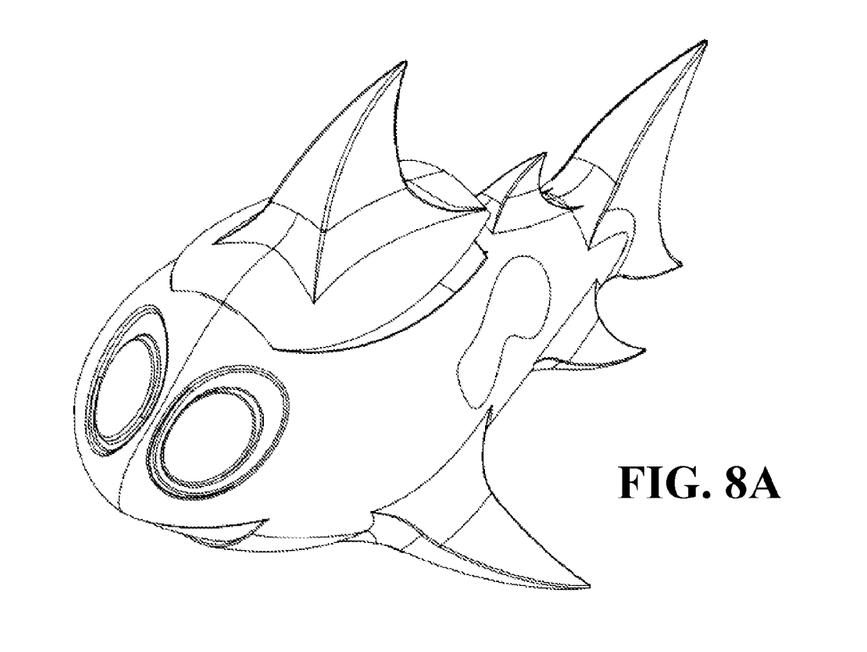
FIG. 8A and FIG. 8B illustrate a slightly opened shark-shaped container.
Figure 8B:
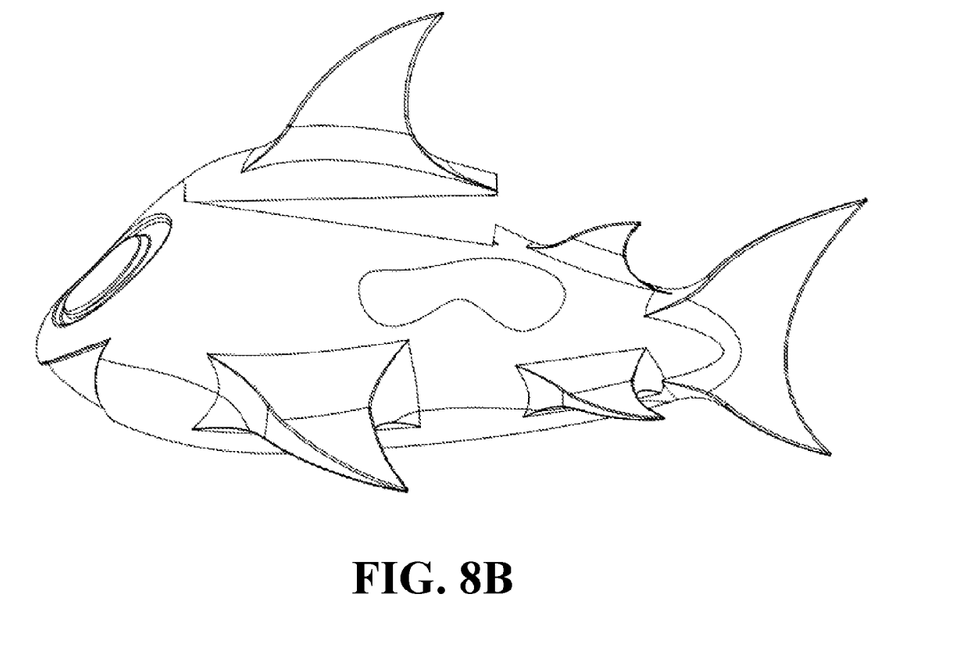

FIG. 1 illustrates one embodiment of a system 11 that rewards a child for behaving well while dining. The system includes at least a container 20 and a plate 10. The container 20 can be in at least a closed state or an open state, and is configured to store a reward 22 for the child. In one example, the volume of the container 20 in its closed state is at least 50 milliliter. The container 20 may be designed according to any configuration that has at least an open state 25 (in which the child can reach the reward 22), and a closed state (in which the child cannot easily reach the reward 22). The container may include a lid 24 fixed on a pivot 26. The lid may switch between the open and closed states using a mechanism 16, which may include one or more of an electrical engine, a spring, a magnet, and/or any other device able to open the container from its closed state. Optionally, the mechanism 16 may enable the parent to open the container 20 even before the plate is empty. The container may have various shapes, such as a dog, an airplane, or a shark. FIG. 6A and FIG. 6B illustrate a slightly opened dog-shaped container. FIG. 7A and FIG. 7B illustrate a slightly opened airplane-shaped container. FIG. 8A and FIG. 8B illustrate a slightly opened shark-shaped container.

Referring back to FIG. 1, the plate 10 is configured to hold food 30, and includes a weighing module 12 and a processor 14. The weighing module 12 is configured to generate indications proportional to the weight of the food 30 on the plate 10. The processor 14 is configured to receive the indications while the container 20 is in its closed state, and to determine, based on analysis of the indications, whether to command the container 20 to switch to its open state 25 when the weight of the food 30 reaches below a predetermined threshold. The communication between the plate and the container may be implemented in various ways, such a wired and/or wireless communication 18 between the processor 14 (optionally located in the plate 10) and the mechanism 16 that is coupled to the container 20. Usually, the container is used to store an object that is different from the food because giving more of the same food would probably not be considered by the child as a reward.

The reward 22 stored in the closed container 20 should not encourage the child to throw the food 30 out of the plate 10 in order to open the container 20. In one embodiment, the system measures the rate of removing the food 30 from the plate 10, which is assumed to be in proportion to the rate of consuming the food 30 by the child. When the rate of removing the food 30 from the plate 10 exceeds a predetermined eating rate threshold, then the processor 14 infers that the child did not eat the food 30 well, and thus does not command 18 the container 20 to switch to its open state when the weight of the food 30 left on the plate 10 reaches the predetermined threshold. Optionally, the processor 14 may be physically located and/or embedded within one or more of the following modules: the plate 10, the mechanism 16, the lid 24, the container 20, another electronic device (such as tablet 46), and/or in another location.

In one embodiment, the analysis of the indications includes calculating the rate of removing the food 30 from the plate 10, referred to as $R_r$. The processor 14 compares $R_r$ with a predetermined max eating rate, referred to as $R_m$, when $R_r<R_m$ the processor 14 commands the container 20 to switch to its open state when the weight of the food 30 reaches below the predetermined threshold, and when $R_r>R_m$ the processor 14 does not command the container 20 to switch to its open state when the weight of the food 30 reaches below the predetermined threshold. Optionally, $R_m$ may be a function of the age of the child. It is noted that herein: a child, a young child, a toddler, and/or a baby—all refer to children aged one to ten years.

Additionally or alternatively, the processor 14 may communicate with two or more containers 20 configured to switch to their open states progressively as the child consumes the food 30. For example, a first container may switch to its open state after the weight of the food decreases in 50%, a second container may switch to its open state after the weight of the food decreases in 75%, and a third container may switch to its open state when the plate is empty.

Figure 2:
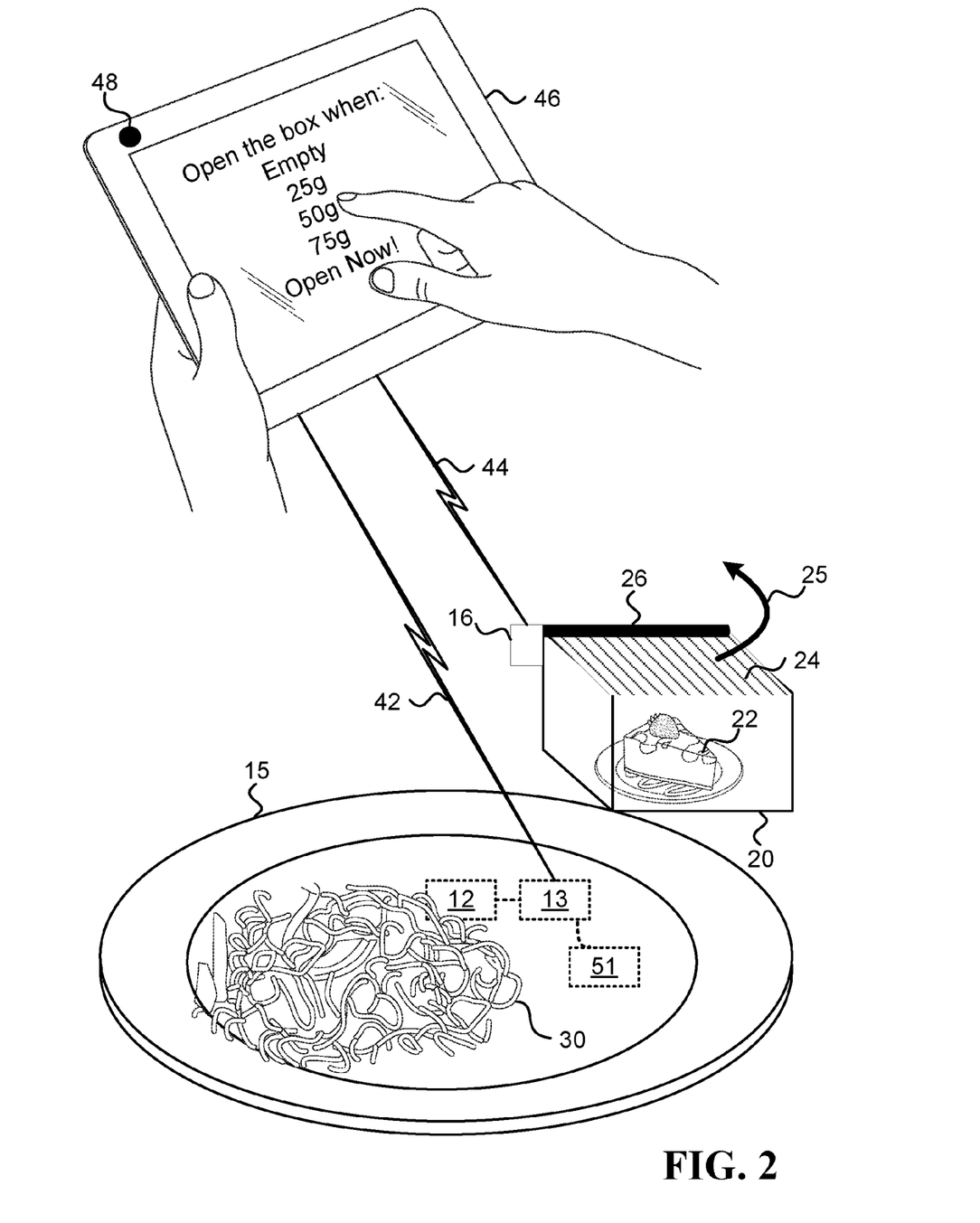
FIG. 2 illustrates one embodiment where the child's parent can use an electronic device (such as a tablet) to set the predetermined threshold.

FIG. 2 illustrates one embodiment where $R_m$ is set by the child's parent via a user interface (such as tablet 46) that includes the functionality of the processor 14 together with additional options, such as selecting the predetermined threshold (e.g., empty, 25 g, 50 g, 75 g, user specific value) and remote opening of the container 20. When the processor is in the tablet 46, the plate 15 may be simplified to include weighing module 12 and communication module 13 to communicate wirelessly 42 with the tablet 46. In this configuration, the tablet 46 commands the mechanism 16 when to open the container 20.

In one embodiment, the system receives from a camera 48 a video of the child while eating from the plate 15, and based on analyzing the video the system sets $R_m$ and/or $R_r$ according to the child's actual eating rate.

In one embodiment, in order to encourage the child to behave well while dining, the processor (14 or tablet 46) receives data from a movement sensor 51 coupled to the plate 15. The processor utilizes the data to infer whether the child flipped the plate 15, and if the plate was flipped then the processor does not command the container 20 to switch to its open state when the weight of the food 30 reaches below the predetermined threshold. When the processor infers, based on the data received from the movement sensor 51, that the plate was not flipped while dining, the processor commands the container 20 to switch to its open state when the weight of the food 30 reaches below the predetermined threshold.

In one embodiment, during a normal eating course while there is still a significant amount of food on the plate, flipping the plate makes the rate of removing the food from the plate ($R_r$) to be greater than the predetermined max eating rate ($R_m$), and therefore the processor does not command the container to switch to its open state when the weight of the food on the plate reaches below the predetermined threshold as a result of flipping the plate. In another embodiment, the decision whether to open the container is not based on $R_r$, and receiving an indication that the plate was flipped is enough to keep the container closed even when the weight of the food on the plate reaches below the predetermined threshold.

It is noted that sentences such as "commanding the container to switch to its open state when the weight of the food on the plate reaches below the predetermined threshold" cover issuing the command zero to three minutes from the moment of reaching the predetermined threshold. In one example, the command is sent immediately upon reaching the predetermined threshold. In another example, an encouraging message is played to the child when reaching the predetermined threshold, and sending the command to open the container while or after playing the encouraging message, such that the container 20 switches to its open state more than thirty seconds after the weight of the food 30 on the plate 10 reached the predetermined threshold. It is further noted that switching the container from a closed state to an opened state is equivalent to moving a lid that covers the opening of the container from a closed state (where the lid closes the container) to an open state (where the lid does not close the container).

In one example, the predetermined threshold is below 100 gram. In another example, the predetermined threshold is below 20 gram. In still another example, the predetermined threshold is below 50% of the initial weight of the food 30. And in still another example, the predetermined threshold is below 10% of the initial weight of the food 30.

The systems may have different mechanical configurations, all of them are intended to be covered by the disclosed embodiments and appended claims. For example, the plate and the container may be stiffly connected as a single piece. Additionally or alternatively, the plate and the container may be two distinct devices that are not physically connected in a fixed manner. Optionally, a short-range communication module may send data from the plate to the container. Optionally, the short-range communication may be wireless communication that utilizes one or more of the following standards: Bluetooth, ZigBee, Near field communication (NFC), RFIC, and Infrared-based transmissions. Additionally or alternatively, the short-range communication may be wired communication.

In one embodiment, the container may be made as a single device, which includes both a box for storing the reward and the electronics for opening the box. Alternatively, the container may be made as a two parts device, where the first part includes the box for storing the reward, which may be washed in a dishwasher, and the second part includes at least some of the electronics, such as the battery, which may be sensitive to the environmental conditions in the dishwasher. Additionally, the second part may be a mount, and the container may be configured to be placed on the mount (that includes a battery and/or an electronic circuit that are not designed for being washed in a dishwasher on a regular basis).

Figure 3:
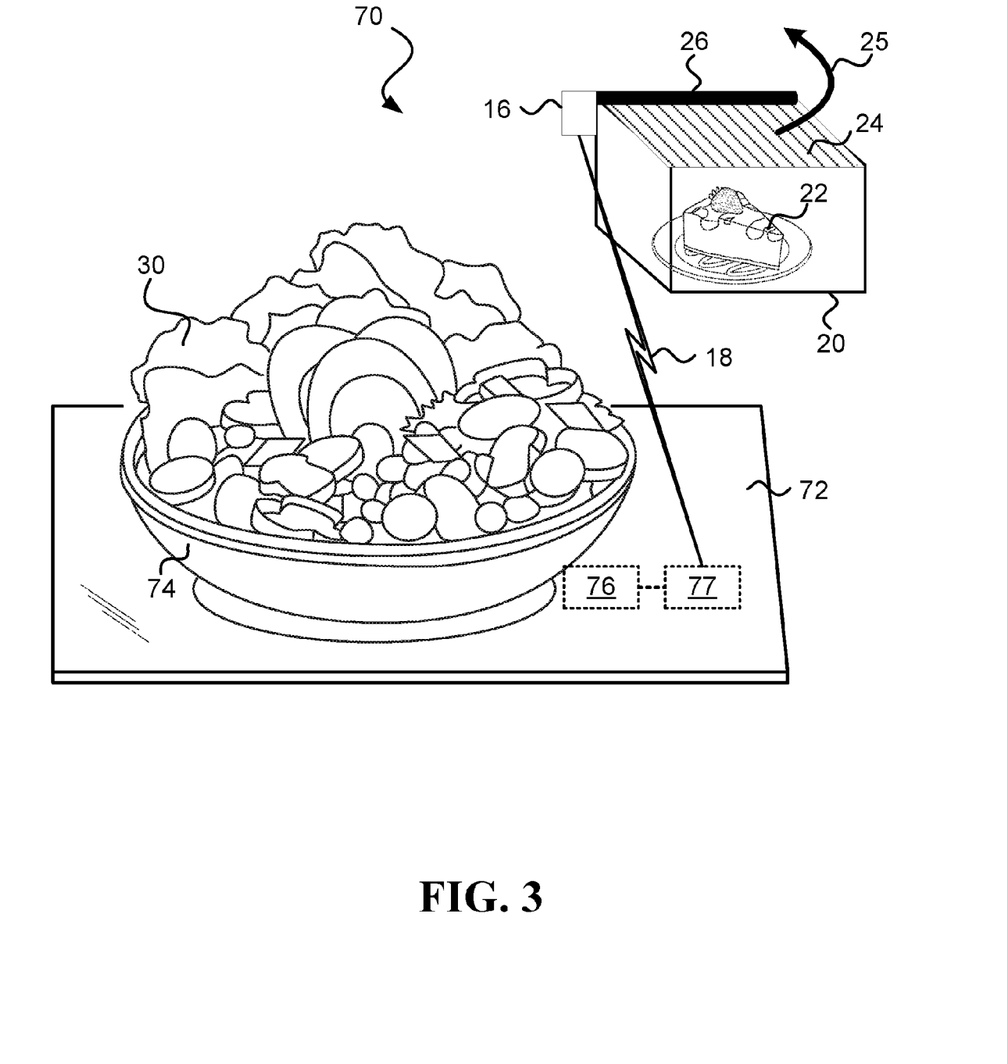
FIG. 3 illustrates one embodiment of system that includes a weighing tray.

FIG. 3 illustrates one embodiment of system 70 that includes a tray 72 configured to hold a plate 74. The tray 72 includes a weighing module 76 and a processor 77, which may be similar to weighing module 12 and a processor 14. Optionally, the tray 72 is integrated with a high chair.

Optionally, the tray 72 is configured to weigh the plate 74 without the food 30, and then to weigh the plate 74 with the food 30 in order to calculate the indications proportional to the weight of the food 30, which may be referred to as tare adjustment feature. Optionally, the system further includes a tare button to measure multiple food items placed on the plate 74 and/or on the tray 72. In this case, the weighing module 76 may be configured to measure the next food item for a predetermined duration after pressing the tare button.

The tray 72 and the container 20 may be produced in various ways. In one embodiment, the tray 72 and the container 20 are stiffly connected as a single piece. In another embodiment, the tray 72 and the container 20 are two distinct devices that are not physically connected in a fixed manner. In one example, the tray 72 and the container 20 communicate using short-range communication modules configured to send data from the tray 72 to the container 20, and optionally also from the container 20 to the tray 72. Optionally, the short-range communication is wireless communication that utilizes one or more of the following standards: Bluetooth, ZigBee, Near field communication (NFC), RFIC, and Infrared based transmissions. Additionally or alternatively, the short-range communication modules are wired communication modules.

Figure 4:
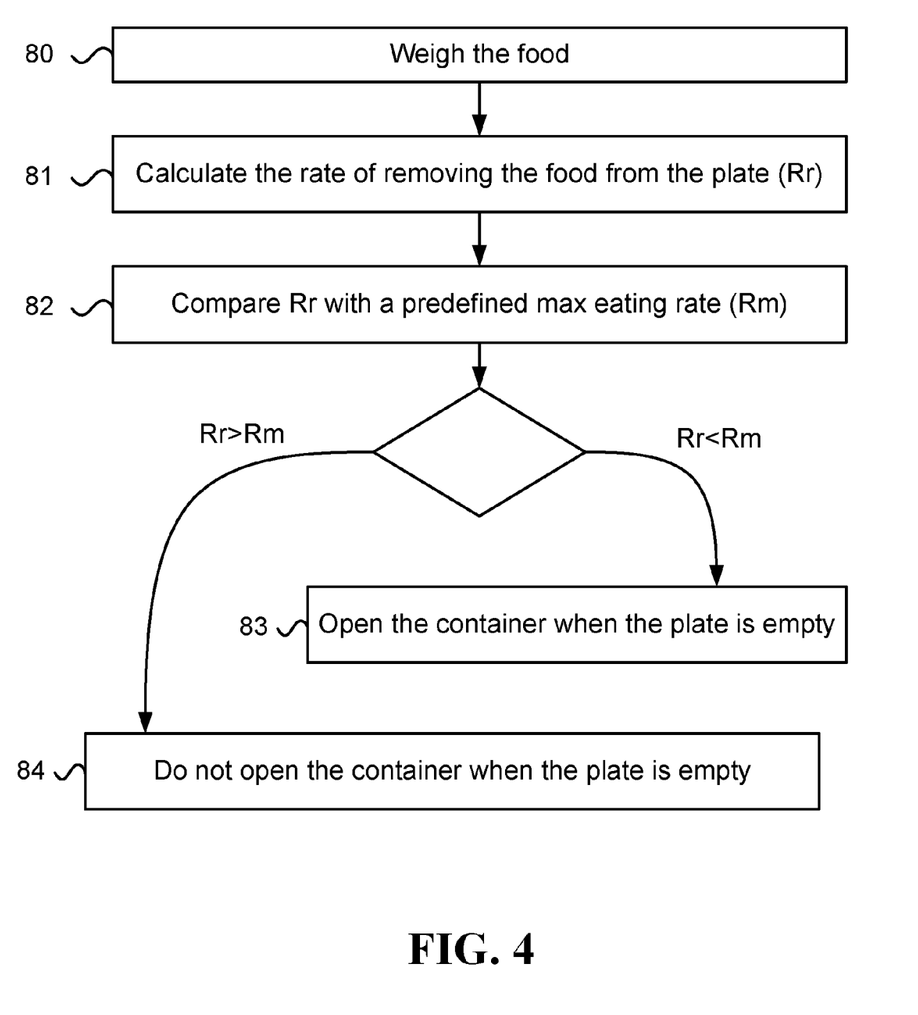
FIG. 4 illustrates one embodiment of a method for rewarding a child for behaving well while dining.

FIG. 4 illustrates one embodiment of a method for rewarding a child for behaving well while dining. The method includes the following steps: In step 80, generating indications proportional to the weight of the food on the plate. In step 81, calculating the rate of removing the food from the plate ($R_r$). In step 82, comparing $R_r$ with a predetermined max eating rate ($R_m$). In step 83, if identifying that $R_r < R_m$, then commanding the container to switch from a closed state to an open state when the weight of the food on the plate reaches below a predetermined threshold. And in step 84, if identifying that $R_r > R_m$, then not commanding the container to switch from the closed state to the open state when the weight of the food on the plate reaches below the predetermined threshold. Optionally, the container is configured to store a reward for the child, and the volume of the container in its closed state is at least 50 milliliter.

Optionally, the method further includes determining $R_m$ as a function of the age of the child. Optionally, the method further includes determining $R_m$ by the child's parent via a user interface that communicates with the container. Optionally, the method further includes: receiving a video of the child while eating from the plate, and setting $R_m$ according to the child's actual eating rate. Optionally, the method further includes: receiving data from a movement sensor coupled to the plate, identifying flipping the plate based on the data, and not commanding the container to switch from the closed state to the open state when the weight of the food on the plate reaches below the predetermined threshold. Optionally, the method further includes: receiving data from a movement sensor coupled to the plate, utilizing the data to identify that the plate was not flipped while dining, and commanding the container to switch from the closed state to the open state when the weight of the food on the plate reaches below the predetermined threshold. Optionally, the method further includes a tray configured to hold the plate.

The tray is programmed to weigh the food by weighing the plate without the food, and then weighing the plate with the food.

In a variation of the embodiment above (not illustrated in the figures), the method includes the following steps: In step 85a, generating a first indication proportional to a first weight of a first food on the plate. In step 85b, calculating a first rate of removing the first food from the plate ($R_{r1}$). In step 85c, comparing $R_{r1}$ with a predetermined max eating rate ($R_m$). In step 85d, identifying that $R_{r1} < R_m$ and commanding the container to switch from a closed state to an open state when the weight of the food on the plate reaches below a predetermined threshold. In step 86a, generating a second indication proportional to a second weight of a second food on the plate. In step 86b, calculating a second rate of removing the second food from the plate ($R_{r2}$). In step 86c, comparing $R_{r2}$ with $R_m$. And in step 86d, identifying that $R_{r2} > R_m$ and not commanding the container to switch from the closed state to the open state when the weight of the food on the plate reaches below the predetermined threshold.

Referring back to FIG. 1, in one embodiment a system configured to reward a child for behaving well while dining, includes: a container 20 comprising an opening; a lid 24 configured to cover or uncover the opening; a plate 10 configured to hold food 30; a weighing module 12 configured to generate indications proportional to the weight of the food 30 on the plate 10; and a processor 14 configured to receive the indications while the lid 24 covers the opening, and to determine, based on analysis of the indications, whether to command a mechanism 16 to move the lid 24 to uncover the opening when the weight of the food 30 reaches below a predetermined threshold. Optionally, the container is used to store an object that is different from the food.

Optionally, the analysis comprises: calculating the rate of removing the food 30 from the plate 10 ($R_r$), comparing $R_r$ with a predetermined max eating rate ($R_m$), when $R_r < R_m$ the processor 14 commands the mechanism 16 to move the lid 24 to uncover the opening when the weight of the food 30 reaches below a predetermined threshold, and when $R_r > R_m$ the processor 14 does not command the mechanism 16 to move the lid 24 to uncover the opening when the weight of the food 30 reaches below the predetermined threshold.

Additionally or alternatively, $R_m$ is a function of the age of the child. It is noted that herein, a child, a young child, a toddler, and/or a baby refer to children aged one to ten years. Additionally or alternatively, $R_m$ may be set by the child's parent via a user interface that may communicate with the mechanism 16. Additionally or alternatively, a computer may receive a video of the child while eating from the plate, and to set $R_m$ according to the child's actual behavior and/or eating rate.

Optionally, the processor is further configured to: receive data from a movement sensor coupled to the plate, identify flipping the plate based on the data, and not commanding the mechanism to move the lid to uncover the opening when the weight of the food on the plate reaches below the predetermined threshold. Additionally or alternatively, the processor is further configured to: receive data from a movement sensor coupled to the plate, utilize the data to identify that the plate was not flipped while dining, and command the mechanism to move the lid to uncover the opening when the weight of the food on the plate reaches below the predetermined threshold.

Optionally, the predetermined threshold is below 100 gram. Optionally, the predetermined threshold is below 20 gram. Optionally, the predetermined threshold is below 50% of the initial weight of the food. Optionally, the predetermined threshold is below 10% of the initial weight of the food.

In one embodiment, the system further includes a tray configured to hold the plate. The tray includes the weighing module and is configured to weigh the plate without the food, and then to weigh the plate with the food. Optionally, the tray may be integrated with a high chair.

Optionally, the weighing module comprises a tare adjustment feature that weighs the plate without the food in order to calculate the indications proportional to the weight of the food on the plate based on the total weight of the plate and the food on the plate. Optionally, the system further includes a tare button to measure multiple food items on the plate. The weighing module may be configured to measure the next food item for a predetermined duration after pressing the tare button.

The system may be designed and built in various ways. Optionally, the tray and the container are stiffly connected as a single piece. Optionally, the tray and the container are two distinct devices that are not physically connected in a fixed manner. Optionally, the system further includes a short-range communication module configured to send data from the tray to the container. Optionally, the short-range communication is wireless communication that utilizes one or more of the following standards: Bluetooth, ZigBee, Near field communication (NFC), RFIC, and Infrared based transmissions. Optionally, the short-range communication module is a wired communication module.

Figure 5:
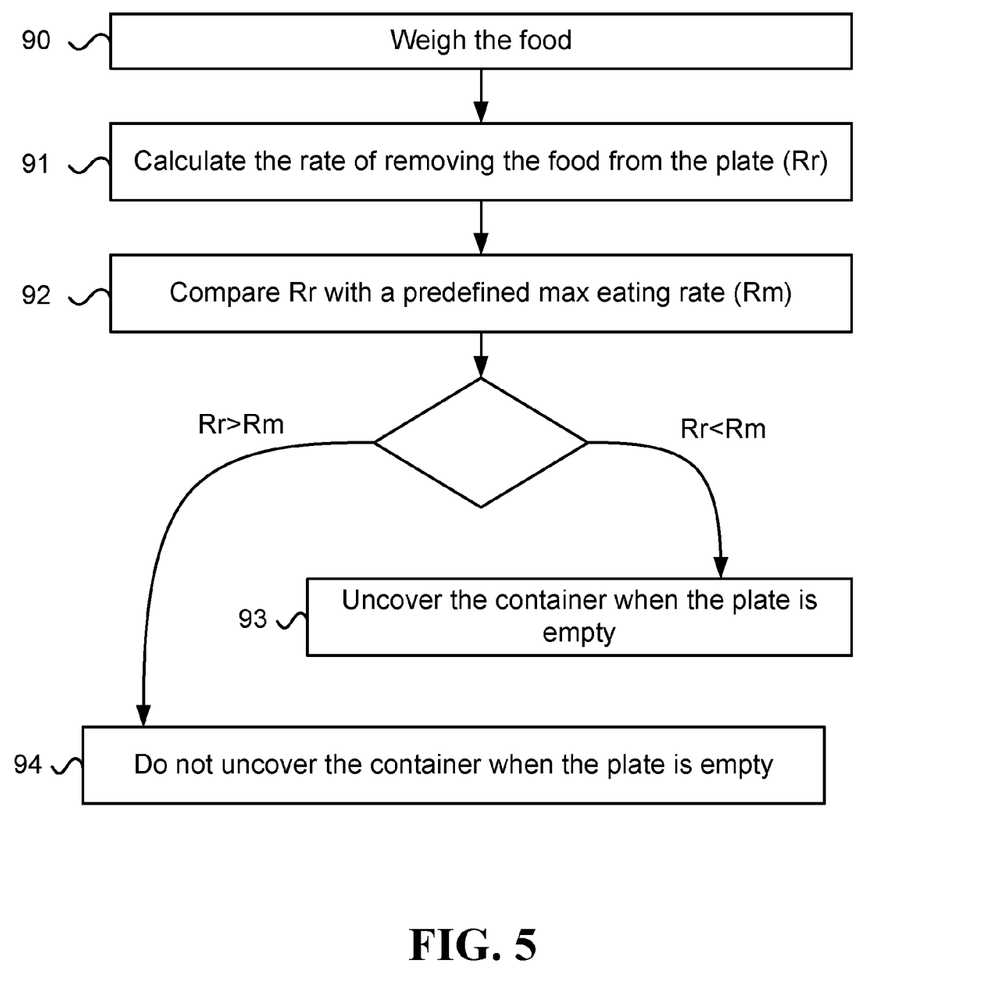
FIG. 5 illustrates another embodiment of a method for rewarding a child for behaving well while dining.

FIG. 5 illustrates one embodiment of a method for rewarding a child for behaving well while dining. The method includes the following steps: In step 90, generating indications proportional to the weight of the food on the plate. In step 91, calculating the rate of removing the food from the plate ($R_r$). In step 92, comparing $R_r$ with a predetermined max eating rate ($R_m$). In step 93, if identifying that $R_r<R_m$, then commanding a lid to uncover a container when the weight of the food on the plate reaches below a predetermined threshold. And in step 94, if identifying that $R_r>R_m$, then not commanding the lid to uncover the container when the weight of the food on the plate reaches below the predetermined threshold. Optionally, the container is configured to store a reward for the child, and the volume of the container in its closed state is at least 50 milliliter.

Optionally, the method further includes determining $R_m$ as a function of the age of the child. Optionally, the method further includes determining $R_m$ by the child's parent via a user interface that communicates with the container. Optionally, the method further includes: receiving a video of the child while eating from the plate, and setting $R_m$ according to the child's actual eating rate.

Optionally, the method further includes: receiving data from a movement sensor coupled to the plate, identifying flipping the plate based on the data, and not commanding the lid to uncover the container when the weight of the food on the plate reaches below the predetermined threshold. Optionally, the method further includes: receiving data from a movement sensor coupled to the plate, utilizing the data to identify that the plate was not flipped while dining, and commanding the lid to uncover the container when the weight of the food on the plate reaches below the predetermined threshold.

In a variation of the embodiment above (not illustrated in the figures), the method includes the following steps: In step 95a, generating a first indication proportional to a first weight of a first food on the plate. In step 95b, calculating a first rate of removing the first food from the plate ($R_{r1}$). In step 95c, comparing $R_{r1}$ with a predetermined max eating rate ($R_m$). In step 95d, if identifying that $R_{r1}<R_m$, then commanding a lid to uncover the opening of the container when the weight of the food on the plate reaches below a predetermined threshold. In step 96a, generating a second indication proportional to a second weight of a second food on the plate. In step 96b, calculating a second rate of removing the second food from the plate ($R_{r2}$). In step 96c, comparing $R_{r2}$ with $R_m$. And in step 96d, if identifying that $R_{r2}>R_m$, then not commanding the lid to uncover the opening of the container when the weight of the food on the plate reaches below the predetermined threshold.

The following options are intended to be combined with the above-described embodiments.

Optionally, a user interface is configured to receive, from a user, a command to keep the lid closed until the weight of the food on the plate reaches below the predetermined threshold. Optionally, the user interface is selected from a group that includes at least one of the following: a smartphone, a tablet, a laptop computer, desktop computer, and a game console. Optionally, the user interface is physically connected to the container.

Optionally, one or more of the methods and/or systems further include a user interface configured to show the child a visual indication of his/her progress towards opening the lid; wherein the visual indication is proportional to the weight of the food on the plate. Optionally, one or more of the methods and/or systems further include an auditory user interface configured to produce a sound that indicates the child about his/her progress towards opening the lid, wherein the pitch of the sound increases as the weight of the food remaining on the plate decreases. Optionally, one or more of the methods and/or systems further include a two-dimensional figure or a three-dimensional figure capable of moving from location A to location B, wherein location B is closer to the container than location A; and a controller configured to move the figure from location A to location B in proportion to the weight of the food, such that the controller commands the figure to be at location A when initializing the system, and commands the figure to be at location B when the weight of the food reaches below the predetermined threshold.

Optionally, the indications proportional to the weight of the food on the plate are received from the weighing module. Additionally or alternatively, the indications proportional to the weight of the food on the plate are received from an electronic device that is not physically connected to the system, and the electronic device communicates with at least one of the weighing module and the opening mechanism. Optionally, the electronic device is selected from a group comprising at least one of the following: a smartphone, a tablet, a laptop computer, desktop computer, and a game console.

Optionally, one or more of the methods and/or systems further include a switch configured to be in at least an 'On' state or an 'Off' state. When the switch is in its 'On' state, the lid covers the opening in a locked manner that cannot be opened easily by a five years old child. And when the switch is in its 'Off' state, the lid cannot enter the locked state. Optionally, the mechanism comprises a spring configured to open the lid in order to switch the lid from the locked state (where the lid covers the opening) to the open state (where the lid does not cover the opening). Optionally, the mechanism comprises a latch configured to lock the lid. Optionally, the mechanism comprises an electromagnetic lock configured to unlock the lid in order to switch the lid from the locked state to an open state.

Optionally, different containers, suitable for different designs, may have different forms, shapes, and/or volumes. For example, the volume of the container may be at least 100 cc, or at least 200 cc, or at least 500 cc.

The lid may have various properties. For example, the lid may be transparent, opaque, may have holes, and/or may seal the container. In one embodiment, the lid may cover the opening of the container firmly enough to prevent the child from reaching an object stored inside the closed container. Alternatively, the lid may cover the opening of the container in a loose manner that enables the child to reach an object stored inside the closed container.

Herein, a predetermined value, such as a predetermined confidence level or a predetermined threshold, is a fixed value and/or a value determined any time before performing a calculation that compares a certain value with the predetermined value. A value is also considered to be a predetermined value when the logic, used to determine whether a threshold that utilizes the value is reached, is known before start of performing computations to determine whether the threshold is reached.

In this description, references to "one embodiment" (and its variations) mean that the feature being referred to may be included in at least one embodiment of the invention. Moreover, separate references to "one embodiment", "some embodiments", "another embodiment", and "still another embodiment" may refer to the same embodiment, may illustrate different aspects of an embodiment, and/or may refer to different embodiments.

The embodiments of the invention may include any variety of combinations and/or integrations of the features of the embodiments described herein. Although some embodiments may depict serial operations, the embodiments may perform certain operations in parallel and/or in different orders from those depicted. Moreover, the use of repeated reference numerals and/or letters in the text and/or drawings is for the purpose of simplicity and clarity and does not in itself dictate a relationship between the various embodiments and/or configurations discussed. The embodiments are not limited in their applications to the order of steps of the methods, or to details of implementation of the devices, set in the description, drawings, or examples. Moreover, individual blocks illustrated in the figures may be functional in nature and therefore may not necessarily correspond to discrete hardware elements. In the claims, the terms "first", "second" and so forth are to be interpreted merely as ordinal designations, and shall not be limited in themselves.

While the methods disclosed herein have been described and shown with reference to particular steps performed in a particular order, it is understood that these steps may be combined, sub-divided, and/or reordered to form an equivalent method without departing from the teachings of the embodiments. Accordingly, unless specifically indicated herein, the order and grouping of the steps is not a limitation of the embodiments. Furthermore, methods and mechanisms of the embodiments will sometimes be described in singular form for clarity. However, some embodiments may include multiple iterations of a method or multiple instantiations of a mechanism unless noted otherwise. For example, when a processor is disclosed in one embodiment, the scope of the embodiment is intended to also cover the use of multiple processors. Certain features of the embodiments, which may have been, for clarity, described in the context of separate embodiments, may also be provided in various combinations in a single embodiment. Conversely, various features of the embodiments, which may have been, for brevity, described in the context of a single embodiment, may also be provided separately or in any suitable sub-combination. Embodiments described in conjunction with specific examples are presented by way of example, and not limitation. Moreover, it is evident that many alternatives, modifications, and variations will be apparent to those skilled in the art. It is to be understood that other embodiments may be utilized and structural changes may be made without departing from the scope of the embodiments. Accordingly, this disclosure is intended to embrace all such alternatives, modifications, and variations that fall within the spirit and scope of the appended claims and their equivalents.

I claim:

1. A system configured to reward a child for behaving well while dining, comprising:
    a container configured to be in at least a closed state or an open state; whereby the container is configured to store a reward for the child, and the volume of the container in its closed state is at least 50 milliliter;
    a plate configured to hold food;
    a weighing module configured to generate indications proportional to the weight of the food on the plate; and
    a processor configured to receive the indications while the container is in its closed state, to calculate a rate of removing the food from the plate ($R_r$) based on the indications, and to compare $R_r$ with a predetermined max eating rate ($R_m$);
    wherein when $R_r < R_m$ the processor commands the container to switch to its open state when the weight of the food on the plate reaches below a predetermined threshold, and when $R_r > R_m$ the processor does not command the container to switch to its open state when the weight of the food on the plate reaches below the predetermined threshold.

2. The system of claim 1 wherein $R_m$ is set by the child's parent via a user interface that communicates with the container.

3. The system of claim 1, wherein the processor is further configured to: receive data from a movement sensor coupled to the plate, identify flipping the plate based on the data, and not commanding the container to switch to its open state when the weight of the food on the plate reaches below the predetermined threshold.

4. The system of claim 1, wherein the processor is further configured to: receive data from a movement sensor coupled to the plate, utilize the data to identify that the plate was not flipped while dining, and command the container to switch to its open state when the weight of the food on the plate reaches below the predetermined threshold.

5. The system of claim 1, wherein the predetermined threshold is below at least one of the following: 100 gram, 20 gram, 50% of the initial weight of the food, and 10% of the initial weight of the food.

6. The system of claim 1, wherein the plate and the container are stiffly connected as a single piece.

7. The system of claim 1, wherein the plate and the container are two distinct devices that are not physically connected in a fixed manner.

8. The system of claim 1, further comprising a tray configured to hold the plate; the tray comprises the weighing module, and the weighing module is configured to weigh the plate without the food, and then to weigh the plate with the food in order to calculate the indications.

9. The system of claim 8, wherein the tray and the container are stiffly connected as a single piece.

10. The system of claim 8, wherein the tray and the container are two distinct devices that are not physically connected in a fixed manner, and further comprising a short-range communication module configured to send data from the tray to the container.

11. The system of claim 8, wherein the tray is integrated with a high chair.

12. A method for rewarding a child for behaving well while dining, comprising:
   generating indications proportional to weight of food on a plate;
   calculating a rate of removing the food from the plate ($R_r$); and
   comparing $R_r$ with a predetermined max eating rate ($R_m$), when $R_r < R_m$ then commanding a container to switch from a closed state to an open state when the weight of the food on the plate reaches below a predetermined threshold, and when $R_r > R_m$ then not commanding the container to switch from the closed state to the open state when the weight of the food on the plate reaches below the predetermined threshold; whereby the container is configured to store a reward for the child, and the volume of the container in its closed state is at least 50 milliliter.

13. The method of claim 12, further comprising setting $R_m$ by the child's parent via a user interface that communicates with the container.

14. The method of claim 12, further comprising receiving data from a movement sensor coupled to the plate, identifying flipping the plate based on the data, and not commanding the container to switch from the closed state to the open state when the weight of the food on the plate reaches below the predetermined threshold.

15. The method of claim 12, further comprising receiving data from a movement sensor coupled to the plate, utilizing the data to identify that the plate was not flipped while dining, and commanding the container to switch from the closed state to the open state when the weight of the food on the plate reaches below the predetermined threshold.

16. The method of claim 12, further comprising a tray configured to hold the plate; wherein the tray is programmed to weigh the food on the plate by weighing the plate without the food and then weighing the plate with the food.

17. A system configured to reward a child for behaving well while dining, comprising:
   a container comprising an opening;
   a lid configured to cover or uncover the opening;
   a plate configured to hold food;
   a weighing module configured to generate indications proportional to the weight of the food on the plate; and
   a processor configured to receive the indications while the lid covers the opening, to calculate a rate of removing the food from the plate ($R_r$), and to compare $R_r$ with a predetermined max eating rate ($R_m$);
   wherein when $R_r < R_m$ the processor commands a motor to move the lid to uncover the opening when the weight of the food on the plate reaches below a predetermined threshold, and when $R_r > R_m$ the processor does not command the motor to move the lid to uncover the opening when the weight of the food on the plate reaches below the predetermined threshold.

18. The system of claim 17, wherein the processor is further configured to: receive data from a movement sensor coupled to the plate, identify flipping the plate based on the data, and not commanding the motor to move the lid to uncover the opening when the weight of the food on the plate reaches below the predetermined threshold.

\* \* \* \* \*